(12) United States Patent
Scott et al.

(10) Patent No.: US 11,657,423 B1
(45) Date of Patent: May 23, 2023

(54) METHOD, APPARATUS, AND COMPUTER PROGRAM PRODUCT FOR VALIDATING ELECTRONIC REBATE CLAIMS

(71) Applicant: MCKESSON CORPORATION, Irving, TX (US)

(72) Inventors: Michael Scott, Irving, TX (US); Seth Phillips, Irving, TX (US); Scott Kemme, Irving, TX (US); Hari Uday, Irving, TX (US); Nicholas Bruni, Irving, TX (US)

(73) Assignee: MCKESSON CORPORATION, Irving, TX (US)

( * ) Notice: Subject to any disclaimer, the term of this patent is extended or adjusted under 35 U.S.C. 154(b) by 476 days.

(21) Appl. No.: 16/836,439

(22) Filed: Mar. 31, 2020

(51) Int. Cl.
*G06Q 30/02* (2023.01)
*G06Q 30/0234* (2023.01)
*G06Q 10/10* (2023.01)
*G16H 10/60* (2018.01)
*G16H 40/20* (2018.01)
*G06F 16/23* (2019.01)
*G16H 70/40* (2018.01)
*G06Q 50/26* (2012.01)
(Continued)

(52) U.S. Cl.
CPC ..... *G06Q 30/0234* (2013.01); *G06F 16/2365* (2019.01); *G06Q 10/10* (2013.01); *G06Q 30/0185* (2013.01); *G06Q 50/265* (2013.01); *G16H 10/60* (2018.01); *G16H 40/20* (2018.01); *G16H 50/70* (2018.01); *G16H 70/40* (2018.01)

(58) Field of Classification Search
CPC ........ G16H 10/60; G06Q 40/08; G06Q 10/10; G06Q 30/0207
See application file for complete search history.

(56) References Cited

U.S. PATENT DOCUMENTS

| 8,635,083 B1 * | 1/2014 | Casu | G06Q 30/06 |
| | | | 705/2 |
| 2012/0053958 A1 * | 3/2012 | Marshall | G06Q 30/02 |
| | | | 705/2 |

(Continued)

OTHER PUBLICATIONS

Drettwan JJ, Kjos AL. An Ethical Analysis of Pharmacy Benefit Manager (PBM) Practices. Pharmacy (Basel). Jun. 14, 2019;7(2):65. doi: 10.3390/pharmacy7020065. PMID: 31207906; PMCID: PMC6631892 (Year: 2019).*

(Continued)

*Primary Examiner* — Joseph D Burgess
(74) *Attorney, Agent, or Firm* — Alston & Bird LLP

(57) ABSTRACT

A method, apparatus and computer program product are provided for providing rebate claim validation. A drug manufacturer or associated computer may receive rebate claims from pharmacy benefit managers (PBMs). The manufacturer should not be obligated to pay the rebate if the associated prescription drug was initially sold by the manufacturer under a discount program such as 340B. However, manufacturers may not be able to discern which rebate claims are associated with a discount program. A service provider utilizes adjudicated prescription claims from a contract pharmacy, and encounter data from a covered entity to validate the rebate claims and indicate to the manufacturer whether a rebate claim is associated with a discount program such as 340B.

23 Claims, 8 Drawing Sheets

(51) Int. Cl.
*G06Q 30/018* (2023.01)
*G16H 50/70* (2018.01)

(56) References Cited

U.S. PATENT DOCUMENTS

2015/0261935 A1* 9/2015 Crockett ................ G06Q 10/10
705/2
2016/0358293 A1* 12/2016 Berger ............... G06Q 30/0207

OTHER PUBLICATIONS iqvia.com, Internet Archive Wayback Machine, Jun. 2, 2013 to Jun. 22, 2020, 2 pages, retrieved from https://web.archive.org/web/20171127104852/https://www.iqvia.com/ on Jun. 25, 2020.

* cited by examiner

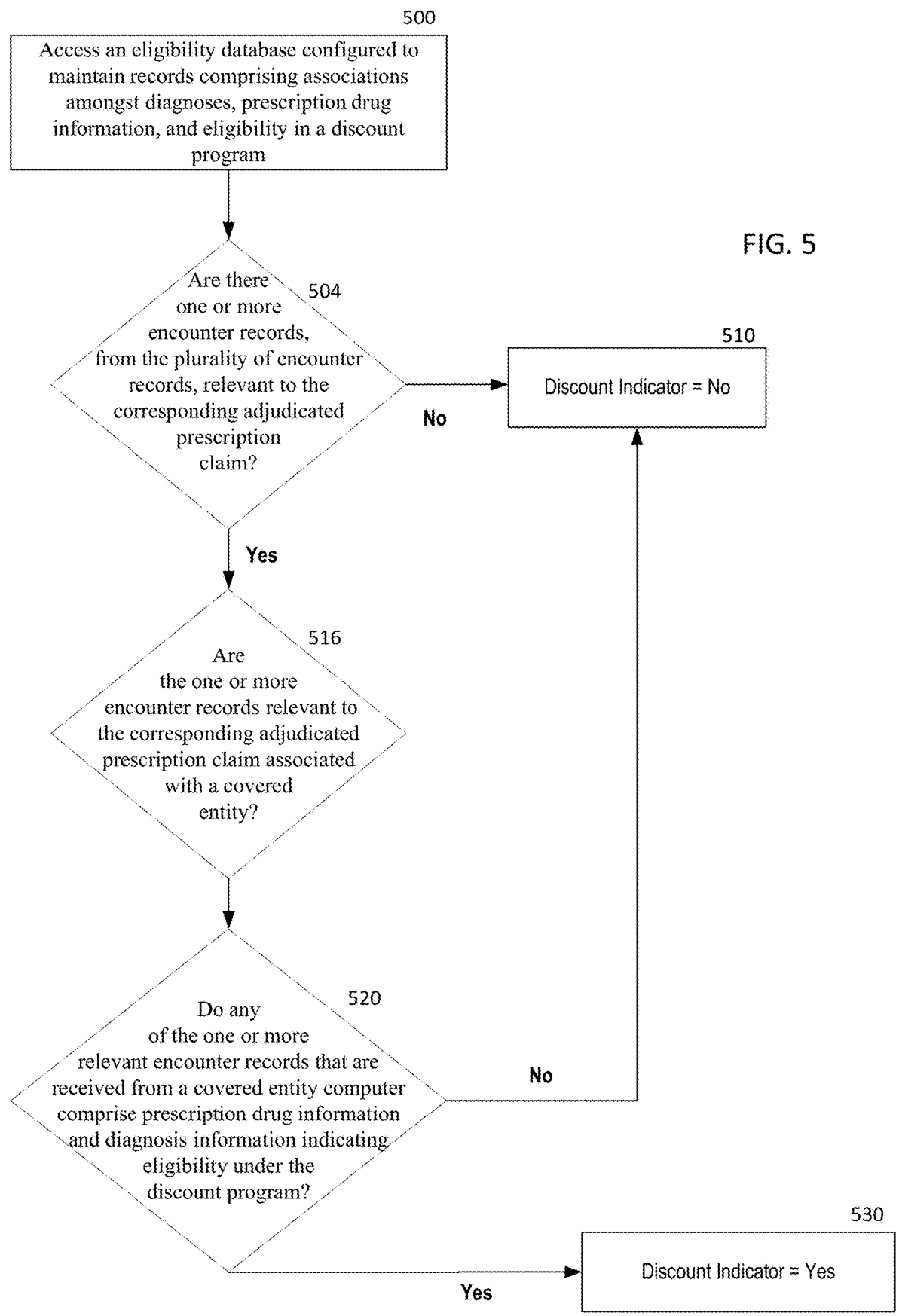

METHOD, APPARATUS, AND COMPUTER PROGRAM PRODUCT FOR VALIDATING ELECTRONIC REBATE CLAIMS

TECHNOLOGICAL FIELD

Embodiments of the present invention relate generally to electronic rebate claims for prescription medication and, more particularly, to methods, apparatuses, and computer program products for validating electronic rebate claims using electronic prescription claims and electronic patient encounter data.

BACKGROUND

Various government-sponsored and non-government-sponsored programs and entities exist for providing reduced costs for prescription products such as prescription medications, medical devices, and other prescription products. Such programs or entities may include, for example, the federal 340B drug pricing program, or "340B program."

The 340B program requires drug manufacturers to provide certain prescription drugs to eligible healthcare centers, clinics, and hospitals (referred to as "covered entities") at a reduced price. This reduced price, sometimes interchangeably referred to as the "340B price," represents a maximum price that a covered entity is required to pay for select prescription drugs dispensed in accordance with the requirements of the 340B program, and is often significantly lower than the Wholesale Acquisition Cost (WAC) price for such drugs.

A covered drug under the 340B program may include, for example, a U.S. Food and Drug Administration (FDA) approved prescription drug, an over-the-counter (OTC) drug that is written on a prescription, and so forth. Covered entities eligible to participate in the 340B program may include non-profit entities and/or entities that focus on treating particular disease conditions. A covered entity may include, for example, federally-qualified health centers, hospitals that treat indigent patients through a disproportionate share hospital (DSH) program, children's hospitals, cancer clinics, family planning projects, state-operated AIDS Drug Assistance Programs (ADAPs), black lung clinics receiving federal funds, and so forth. Prescription drug purchases at the 340B price represent a significant cost savings over the typical costs for such drugs. The cost savings can, in turn, be passed on to patients, thereby reducing the overall cost of patient care to both healthcare providers and patients. In many cases, the manufacturer of the prescription drug agrees to provide prescription medication covered under the 340B program at a discounted rate so the prescription may be made available to a patient and the 340B price.

In separate programs from the 340B program, certain drug manufacturers may also offer rebates or incentives for their prescription drugs. Such incentives may be referred to as a coupon, voucher, discount, rebate, and/or the like. In certain implementations, rebates may be provided in the form of a targeted co-pay that the manufacturer desires the patient to pay out-of-pocket to purchase the prescription. When a prescription benefit manager (PBM) receives and processes a prescription claim associated with a prescription drug for which manufacturer rebates are available, the PBM submits a rebate claim to the manufacturer. In many instances, policies relating to the rebates and/or incentive programs are set forth in a contract between the manufacturer and PBM, and many such contracts prevent the rebate in the event the prescription is obtained under the 340B program at the 340B price. However, due to complexities in some claims processing systems, and within the 340B program and associated supporting technology, the manufacturer often cannot discern whether a prescription for which a rebate claim is made by the PBM was a prescription sold at a 340B price, or if the prescription was prescribed and sold outside of the 340B program. If a manufacturer allows a rebate for a prescription that was sold under the 340B program, the manufacturer may unknowingly and systematically enable a "duplicate discount," the first discount occurring by providing the prescription drug at the discounted 340B price, and the second discount occurring by honoring a rebate or incentive credited to the PBM.

BRIEF SUMMARY

Methods, apparatuses, and computer program products are therefore provided for validating electronic rebate claims using electronic prescription claims and electronic patient encounter records.

An apparatus is provided. The apparatus may include at least one processor and at least one memory including computer program code, the at least one memory and the computer program code configured to, with the processor, cause the apparatus to at least receive an indication of a rebate claim validation request from a rebate facilitation computer, the rebate claim validation request comprising requestor-provided prescription drug information.

The at least one memory and computer program code may be further configured to receive an indication of a plurality of adjudicated prescription claims received from a plurality of pharmacy computers, wherein an adjudicated prescription claim comprises pharmacy-provided prescription drug information and patient information associated with a patient with whom a respective adjudicated prescription claim is associated.

In certain embodiments, the at least one memory and computer program code may be further configured to determine a corresponding adjudicated prescription claim that corresponds with the rebate claim validation request, from the plurality of adjudicated prescription claims, by matching one or more of the requestor-provided prescription drug information to one or more pharmacy-provided prescription drug information;

In certain embodiments, the at least one memory and computer program code may be further configured to receive a plurality of encounter records from a healthcare entity computer, an encounter record comprising a medication identifier of a prescribed medication, diagnosis information, and patient information.

In certain embodiments, the at least one memory and computer program code may be further configured to generate, by at least accessing the plurality of encounter records, a discount indicator indicating whether the corresponding adjudicated prescription claim is associated with a discount program.

The at least one memory and computer program code may be further configured to cause transmission of a rebate claim validation response to the rebate facilitation computer, the rebate claim validation response comprising the discount indicator and information associating the rebate claim validation response to the rebate claim validation request.

The at least one memory and computer program code may be further configured to cause transmission of information relating to the rebate claim validation request to a covered entity computer.

A method is provided, including receiving an indication of a rebate claim validation request from a rebate facilitation computer, the rebate claim validation request comprising requestor-provided prescription drug information. The method may further include receiving an indication of a plurality of adjudicated prescription claims received from a plurality of pharmacy computers, wherein an adjudicated prescription claim comprises pharmacy-provided prescription drug information and patient information associated with a patient with whom a respective adjudicated prescription claim is associated.

The method may further include determining a corresponding adjudicated prescription claim that corresponds with the rebate claim validation request, from the plurality of adjudicated prescription claims, by matching one or more of the requestor-provided prescription drug information to one or more pharmacy-provided prescription drug information. In certain embodiments, the method includes receiving a plurality of encounter records from a healthcare entity computer, an encounter record comprising a medication identifier of a prescribed medication, diagnosis information, and patient information.

In some embodiments, the method includes generating, by at least accessing the plurality of encounter records, a discount indicator indicating whether the corresponding adjudicated prescription claim is associated with a discount program. The method further includes, causing transmission of a rebate claim validation response to the rebate facilitation computer, the rebate claim validation response comprising the discount indicator and information associating the rebate claim validation response to the rebate claim validation request.

The method may further include causing transmission of information relating to the rebate claim validation request to a covered entity computer.

A computer program product is provider, comprising at least one non-transitory computer-readable storage medium having computer-executable program code instructions stored therein, the computer-executable program code instructions comprising program code instructions to receive an indication of a rebate claim validation request from a rebate facilitation computer, the rebate claim validation request comprising requestor-provided prescription drug information.

The computer-executable program code instructions may further include program code instructions to receive an indication of a plurality of adjudicated prescription claims received from a plurality of pharmacy computers, wherein an adjudicated prescription claim comprises pharmacy-provided prescription drug information and patient information associated with a patient with whom a respective adjudicated prescription claim is associated.

The computer-executable program code instructions may further include program code instructions to determine a corresponding adjudicated prescription claim that corresponds with the rebate claim validation request, from the plurality of adjudicated prescription claims, by matching one or more of the requestor-provided prescription drug information to one or more pharmacy-provided prescription drug information;

The computer-executable program code instructions may further include program code instructions to receive a plurality of encounter records from a healthcare entity computer, an encounter record comprising a medication identifier of a prescribed medication, diagnosis information, and patient information.

In certain embodiments, the computer-executable program code instructions may further include program code instructions to generate, by at least accessing the plurality of encounter records, a discount indicator indicating whether the corresponding adjudicated prescription claim is associated with a discount program.

The computer-executable program code instructions may further include program code instructions to cause transmission of a rebate claim validation response to the rebate facilitation computer, the rebate claim validation response comprising the discount indicator and information associating the rebate claim validation response to the rebate claim validation request.

The computer-executable program code instructions may further include program code instructions to cause transmission of information relating to the rebate claim validation request to a covered entity computer.

In certain embodiments, the discount program is the 340B program, and the discount indicator indicates whether or not the corresponding adjudicated prescription claim reflects 340B pricing under the 340B program.

According to certain embodiments, generating the discount indicator comprises determining whether there are one or more relevant encounter records from the plurality of encounter records that comprise patient information associated with the patient information of the corresponding adjudicated prescription claim, and comprise prescription drug information consistent with the pharmacy-provided prescription drug information of the corresponding adjudicated prescription claim, and in an instance it is determined there are no relevant encounter records from the plurality of encounter records that comprise patient information associated with the patient information of the corresponding adjudicated prescription claim, and comprise prescription drug information consistent with the pharmacy-provided prescription drug information of the corresponding adjudicated prescription claim, generating the discount indicator to indicate the corresponding adjudicated prescription claim is not associated with a discount program.

In an instance it is determined there are one or more relevant encounter records from the plurality of encounter records that comprise patient information associated with the patient information of the corresponding adjudicated prescription claim, generating the discount indicator may further comprise accessing an eligibility database configured to maintain records comprising associations amongst diagnoses, prescription drug information, and eligibility in a discount program. Based on the associations amongst diagnoses, prescription drug information, and discount program eligibility, generating the discount indicator includes determining whether any of the one or more relevant encounter records are associated with a covered entity and comprise prescription drug information and diagnosis information indicating eligibility under the discount program.

In an instance one or more of the one or more relevant encounter records are associated with the covered entity comprise prescription drug information and diagnosis information indicating eligibility under the discount program, the discount indicator may be generated to indicate the corresponding adjudicated prescription claim is associated with a discount program.

In an instance none of the one or more relevant encounter records are associated with the covered entity comprise prescription drug information and diagnosis information indicating eligibility under the discount program, generating the discount indicator to indicate the corresponding adjudicated prescription claim is not associated with a discount program.

In certain embodiments, determining whether any of the one or more relevant encounter records are associated with a covered entity may include determining whether the healthcare entity computer from which the one or more relevant encounter records originated are associated with the covered entity.

In certain embodiments determining whether any of the one or more relevant encounter records are associated with a covered entity comprises determining whether a prescriber associated with the one or more relevant encounter records is associated with the covered entity.

An apparatus is provided, including means for receiving an indication of a rebate claim validation request from a rebate facilitation computer, the rebate claim validation request comprising requestor-provided prescription drug information. The apparatus may further include means for receiving an indication of a plurality of adjudicated prescription claims received from a plurality of pharmacy computers, wherein an adjudicated prescription claim comprises pharmacy-provided prescription drug information and patient information associated with a patient with whom a respective adjudicated prescription claim is associated.

The apparatus may further include means for determining a corresponding adjudicated prescription claim that corresponds with the rebate claim validation request, from the plurality of adjudicated prescription claims, by matching one or more of the requestor-provided prescription drug information to one or more pharmacy-provided prescription drug information. In certain embodiments, the apparatus may include means for receiving a plurality of encounter records from a healthcare entity computer, an encounter record comprising a medication identifier of a prescribed medication, diagnosis information, and patient information.

In some embodiments, the apparatus may further include means for generating, by at least accessing the plurality of encounter records, a discount indicator indicating whether the corresponding adjudicated prescription claim is associated with a discount program. The apparatus may further include means for causing transmission of a rebate claim validation response to the rebate facilitation computer, the rebate claim validation response comprising the discount indicator and information associating the rebate claim validation response to the rebate claim validation request.

The apparatus may further include means for causing transmission of information relating to the rebate claim validation request to a covered entity computer.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the disclosure in any way. It will be appreciated that the scope of the disclosure encompasses many potential embodiments, some of which will be further described below, in addition to those here summarized.

BRIEF DESCRIPTION OF THE SEVERAL VIEWS OF THE DRAWINGS

Figure 2A:
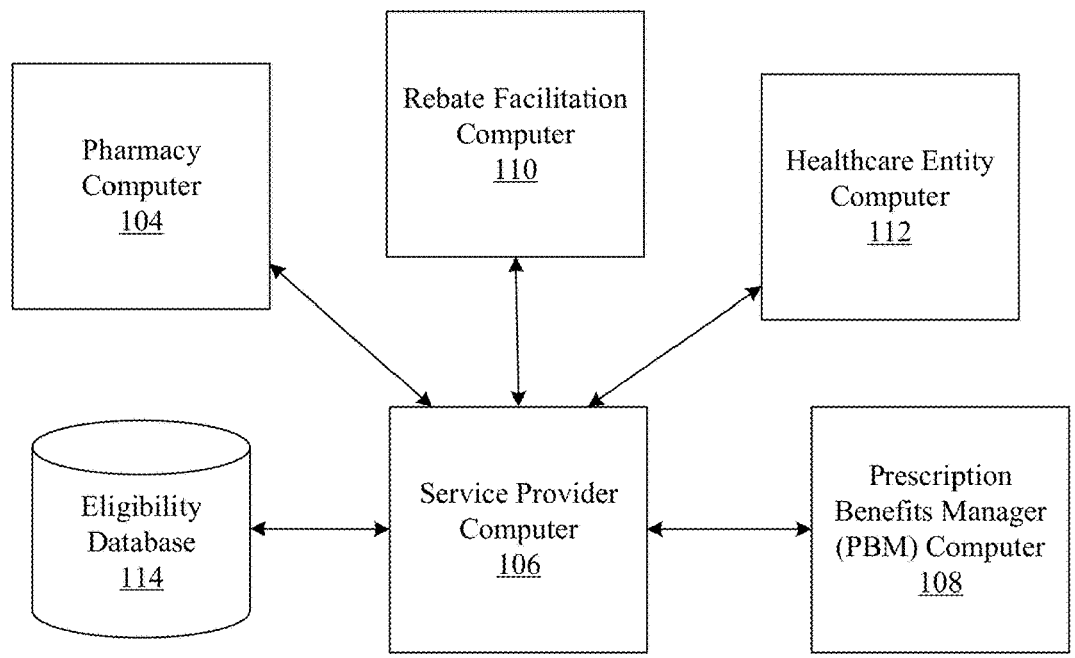
Figure 2B:
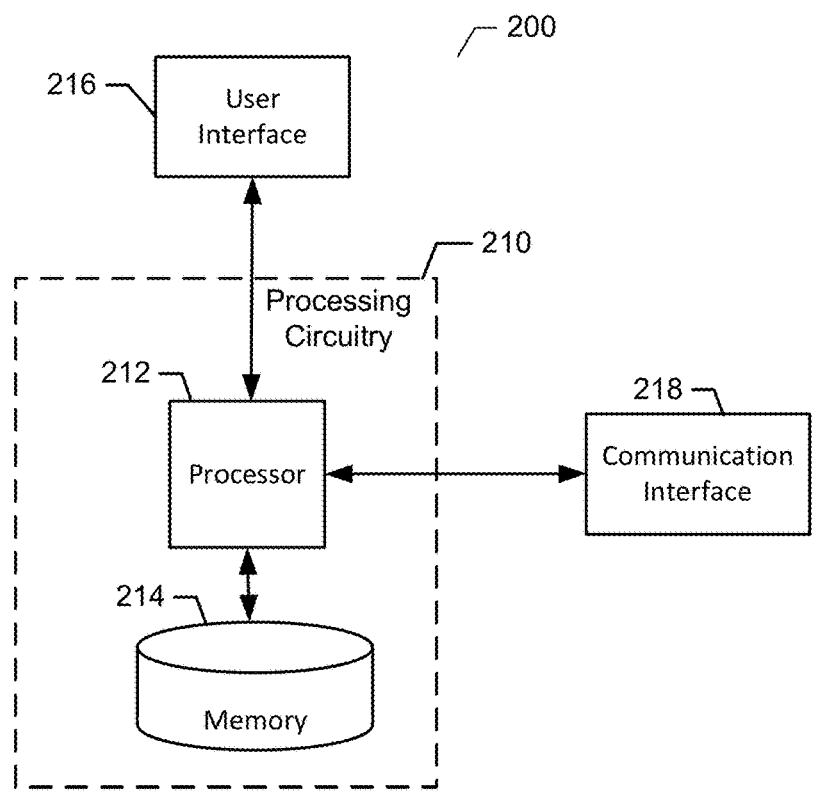
Figure 3:
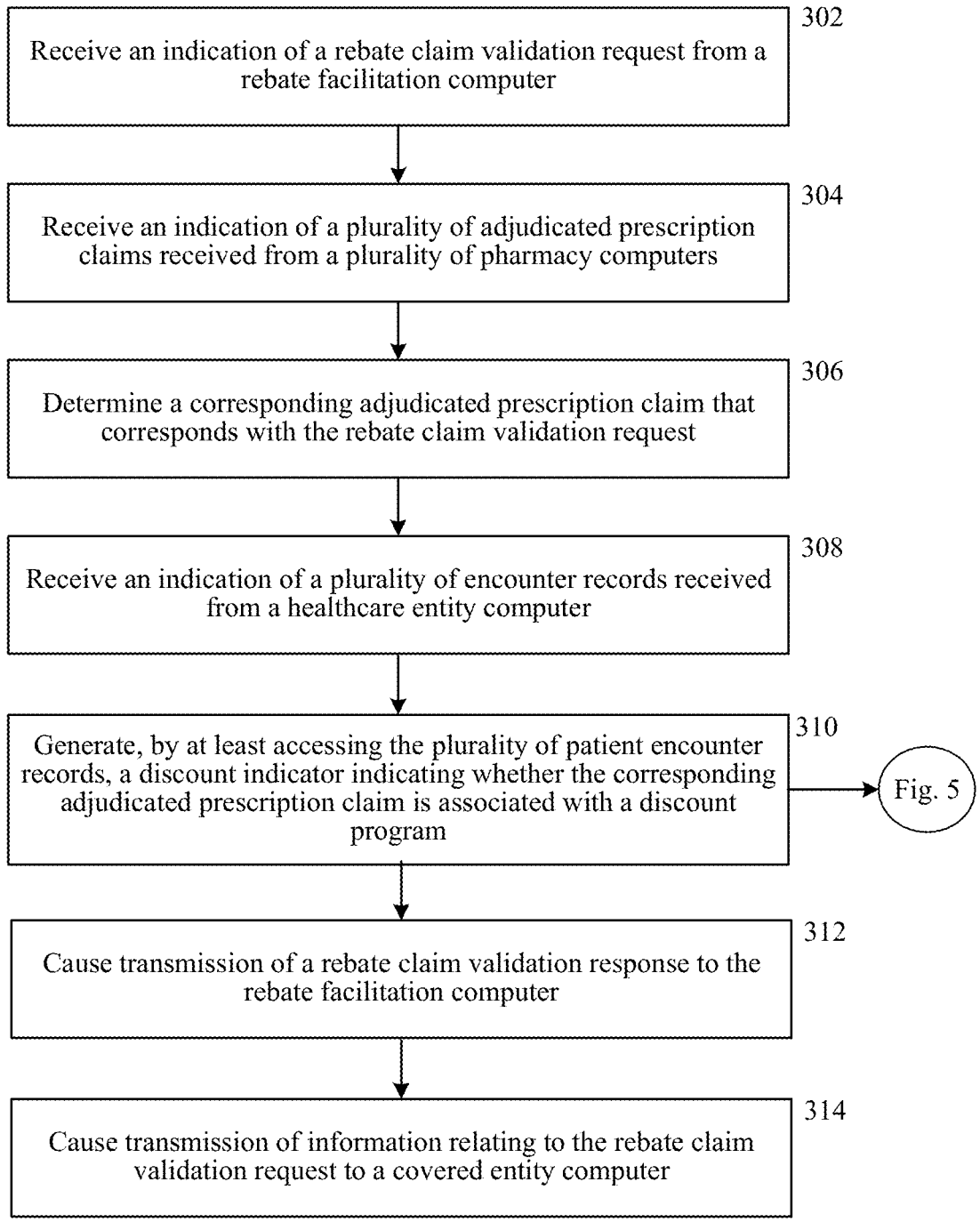
Figure 4:
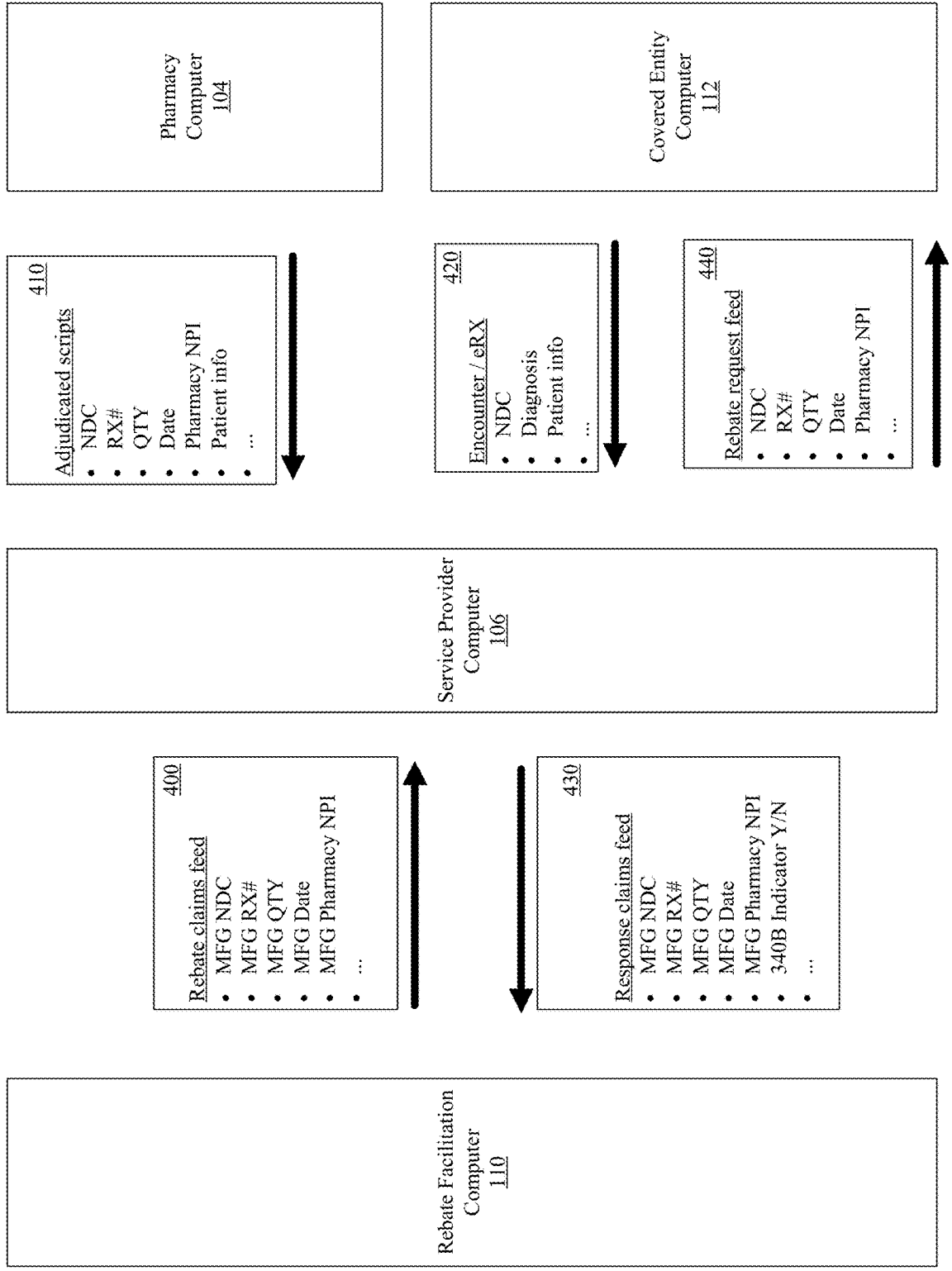

Having thus described embodiments of the invention in general terms, reference will now be made to the accompanying drawings, which are not necessarily drawn to scale, and wherein:

FIGS. 1A-1D and FIG. 2A provide example overviews of a system that can be used to practice some example embodiments described herein;

FIG. 2B is an exemplary schematic diagram of an apparatus in accordance with some example embodiments;

FIG. 3 is a flowchart of operations that may be performed in accordance with some example embodiments;

FIG. 4 is an exemplary diagram illustrating the flow of data in accordance with some example embodiments; and FIG. 5 is a flowchart of operations that may be performed in accordance with some example embodiments.

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, where a computing device is described to receive data from another computing device, it will be appreciated that the data may be received directly from the other computing device and/or may be received indirectly via one or more intermediary computing devices, such as, for example, one or more servers, relays, routers, network access points, and/or the like. Similarly, where a computing device is described herein to transmit data to another computing device, it will be appreciated that the data may be sent directly to the other computing device or may be sent to the other computing device via one or more interlinking computing devices, such as, for example, one or more servers, relays, routers, network access points, and/or the like.

Figure 1A:
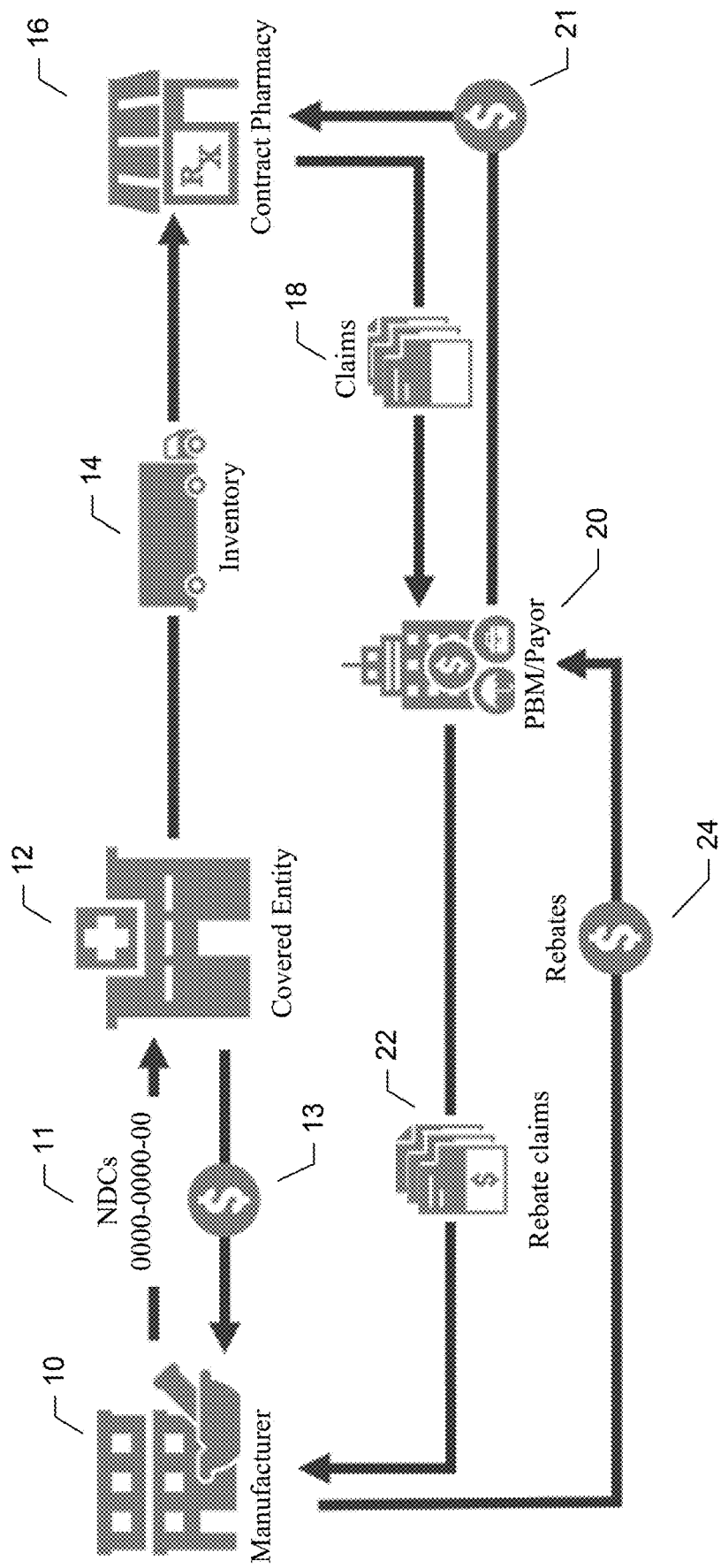

FIG. 1A is an overview of a system that can be used to provide 340B pricing, adjudicate prescription claims, facilitate submission and processing of rebate claims, and/or the like, according to certain example embodiments described herein. A drug manufacturer 10, or "manufacturer," provides certain prescription drugs, such as those having National Drug Codes (NDCs) 11 specified by the 340B program, at a discount to a covered entity, such as covered entity 12. As illustrated by indicator 13, the covered entity 12 pays the manufacturer 10 the discounted 340B price, for the medication. An inventory 14 of prescription drugs may be distributed to a contract pharmacy, such as contract pharmacy 16, and especially allocated for prescriptions written by the covered entity 12 under the 340B program. In this regard, the contract pharmacy 16 may be contracted with the covered entity 12 to dispense the 340B prescription drugs under the program, to patients who are prescribed the prescription drugs by the covered entity 12.

The contract pharmacy 16 may submit prescription claims 18 to the patient's PBM 20, or payor, and the contract pharmacy 16 may be paid, as shown by indicator 21 according to the adjudicated claims. The PBM 20 may further submit rebate claims 22 to the manufacturer 10, and the manufacturer 10 may pay a rebate 24 (e.g., incentive) to the PBM 20.

At least the covered entity 12 and contract pharmacy 14 (in addition to the patient) benefit from the 340B program. The covered entity 12 purchases the prescription drugs from the manufacturer 10 at a discount, and allocates the prescription drugs to a contract pharmacy 14 for the contract pharmacy to dispense. The contract pharmacy 14 sends revenue from 340B prescriptions to the covered entity 12, and receives a dispensing fee payable by the covered entity 12. Due to at least the dispensing fees, the contract pharmacy 14, in some examples, may profit more from a prescription transaction conducted in accordance with the 340B program, in comparison to other prescription transactions conducted outside of the 340B program. The covered entity 12 may benefit by purchasing the prescription drugs at the discounted 340B price, and receiving the associated revenue from the pharmacy. In order to maintain eligibility as a covered entity, and continue to benefit from the 340B program, the covered entity 12 should adhere to complex guidelines when prescribing the medication to a patient under the 340B program. For example, certain requirements relating to the patient, diagnosis(es), prescribed medication, and/or the like, should be satisfied for a prescription written by the covered entity 12 to qualify under the 340B program. In order to maintain their status as a contract pharmacy, the contract pharmacy 14 should also adhere to the rules set forth by the program, namely, dispensing the drugs allocated to the 340B program to qualified patients who were prescribed the medication by a covered entity 12. Accordingly, both the covered entity 12 and contract pharmacy are motivated to adhere to the complex regulations defined by the 340B program in order to remain in the program and benefit from the program as described above.

Figure 1B:
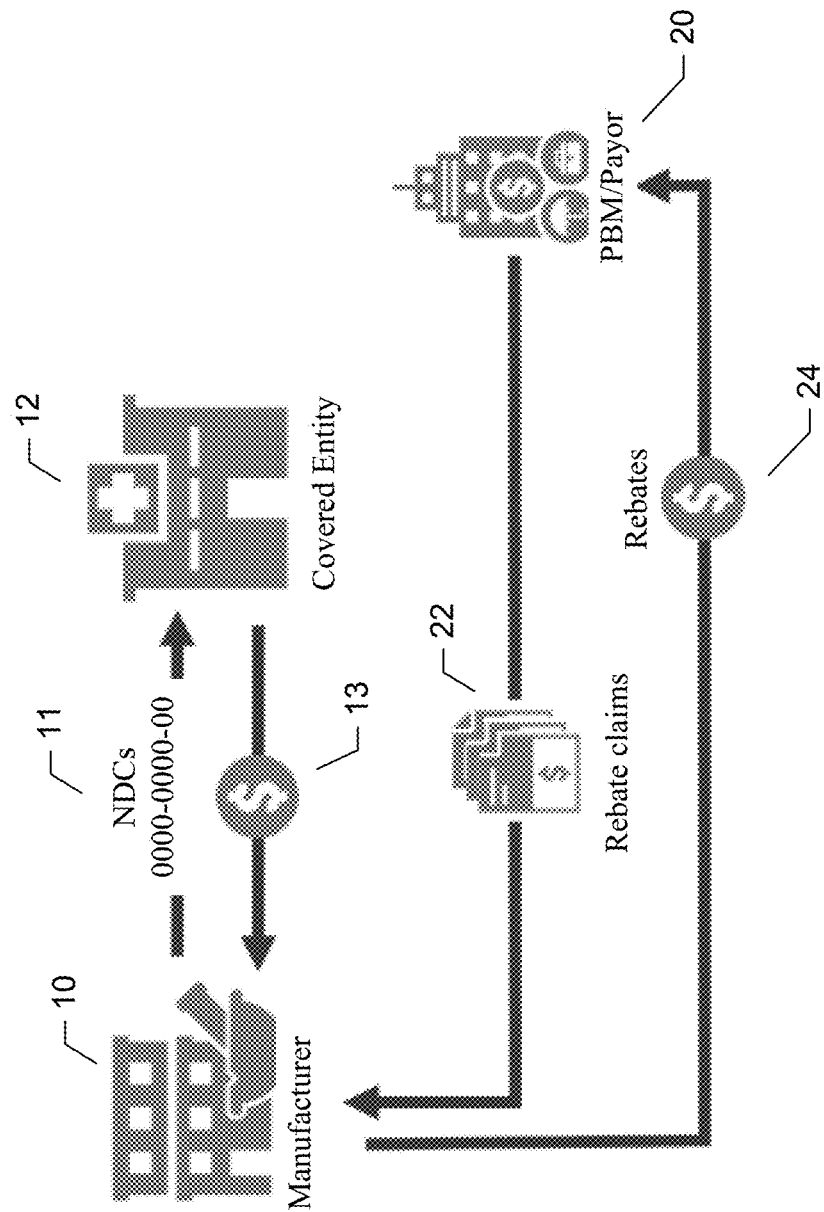

In addition to the above described complexities, the 340B program introduces complexities for the drug manufacturer, such as manufacturer 10. FIG. 1B replicates portions of FIG. 1A, but illustrates that in certain scenarios, the manufacturer 10 may not have insight as to which pharmacies are filling the 340B prescriptions, or may not have access to information regarding prescription claims made to the PBM 20, nor where the prescription claims originated. In many instances, the manufacturer 10 may have information regarding what quantity of particular prescription drugs they sell under the 340B program and distribute to covered entities 12. The manufacturer 10 may also have access to information regarding the PBM 20 and the rebate claims 22 the PBM 20 submits to the manufacturer, but may have no way of reconciling the rebate claims against the quantities of the prescription drug sold under the 340B program. In this regard, the manufacturer 10 may have no means of enforcing its contracts with the PBM 20 with regard to preventing duplicate discounts (crediting rebates/incentives on prescriptions provided under the 340B program).

Figure 1C:
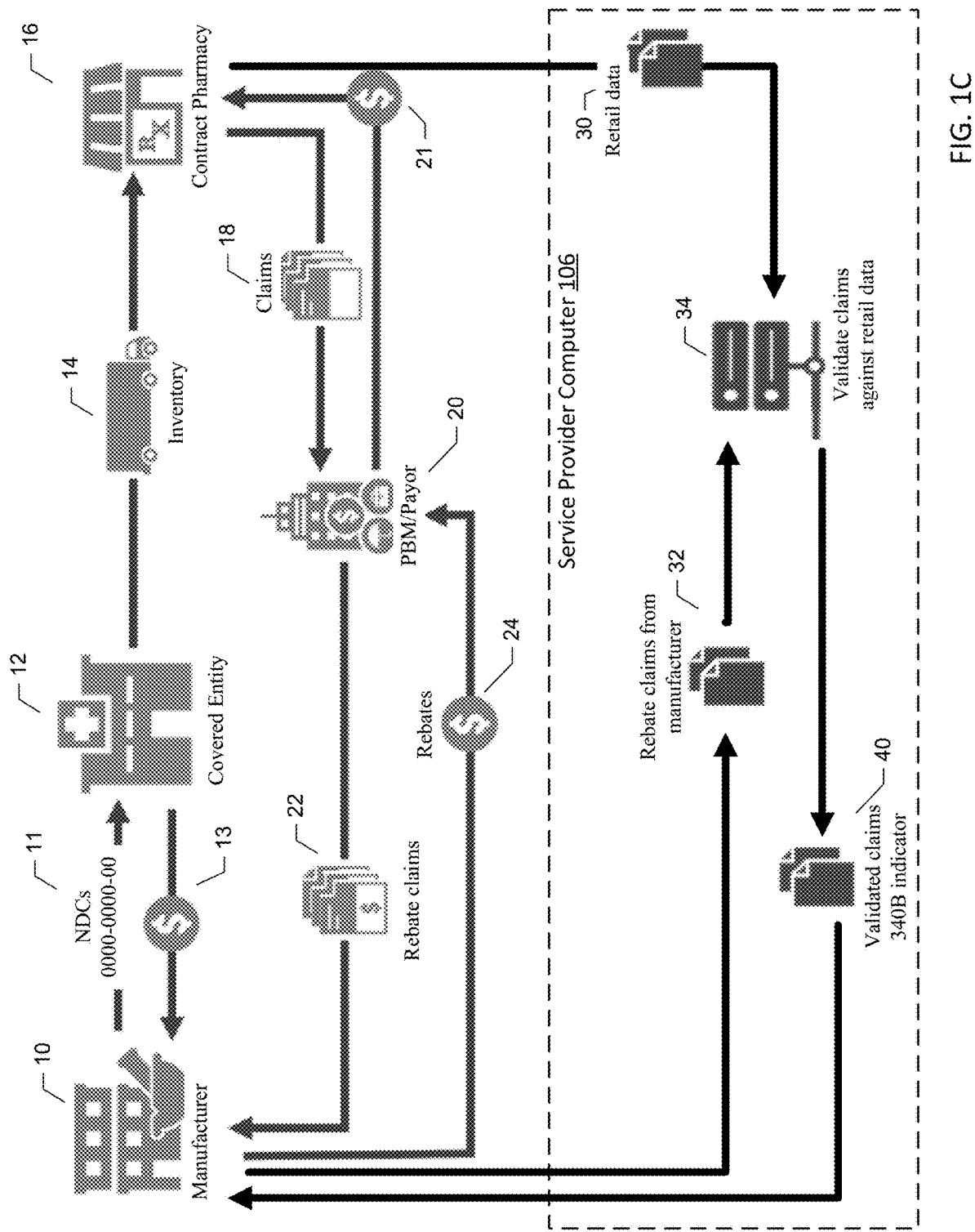

FIG. 1C illustrates how a service provider computer 106, indicated by a dashed line, may alleviate or reduce at least some of the issues described above, according to example embodiments. The service provider computer 106 and associated operations are described in further detail below. As illustrated in FIG. 1C, the service provider computer 106 may receive retail data 30 from pharmacies such as the contract pharmacy 16. The retail data may include, for example adjudicated prescription claims such as those returned by the PBM 20 to the contract pharmacy 16. The manufacturer 10 may forward rebate claims 32, it receives from the PBM 20, or data associated therewith (such as rebate claim validation requests), to the service provider computer 106. The service provider computer 106 may validate the rebate claims against the retail data 34 to determine if a rebate claim is associated with a prescription filled under the 340B program. Accordingly, the service provider computer 106 may return a validated rebate claim 40, including a 340B indicator and/or discount indicator, to the manufacturer 10. The 340B indicator, or discount indicator, may indicate to the manufacturer 10 whether a rebate claim is associated with a prescription drug sold at a discount, such as under the 340B program. Accordingly, it will be appreciated that although the 340B program is referenced frequently herein, certain example embodiments may be configured to determine and indicate whether a prescription drug was sold at a discount in accordance with any other discount program and/or regulated program. For example, legislation and/or regulations could evolve such that the program is rebranded or renamed, and certain example embodiments may be configured to validate rebate claims based on eligibility with such programs.

Figure 1D:
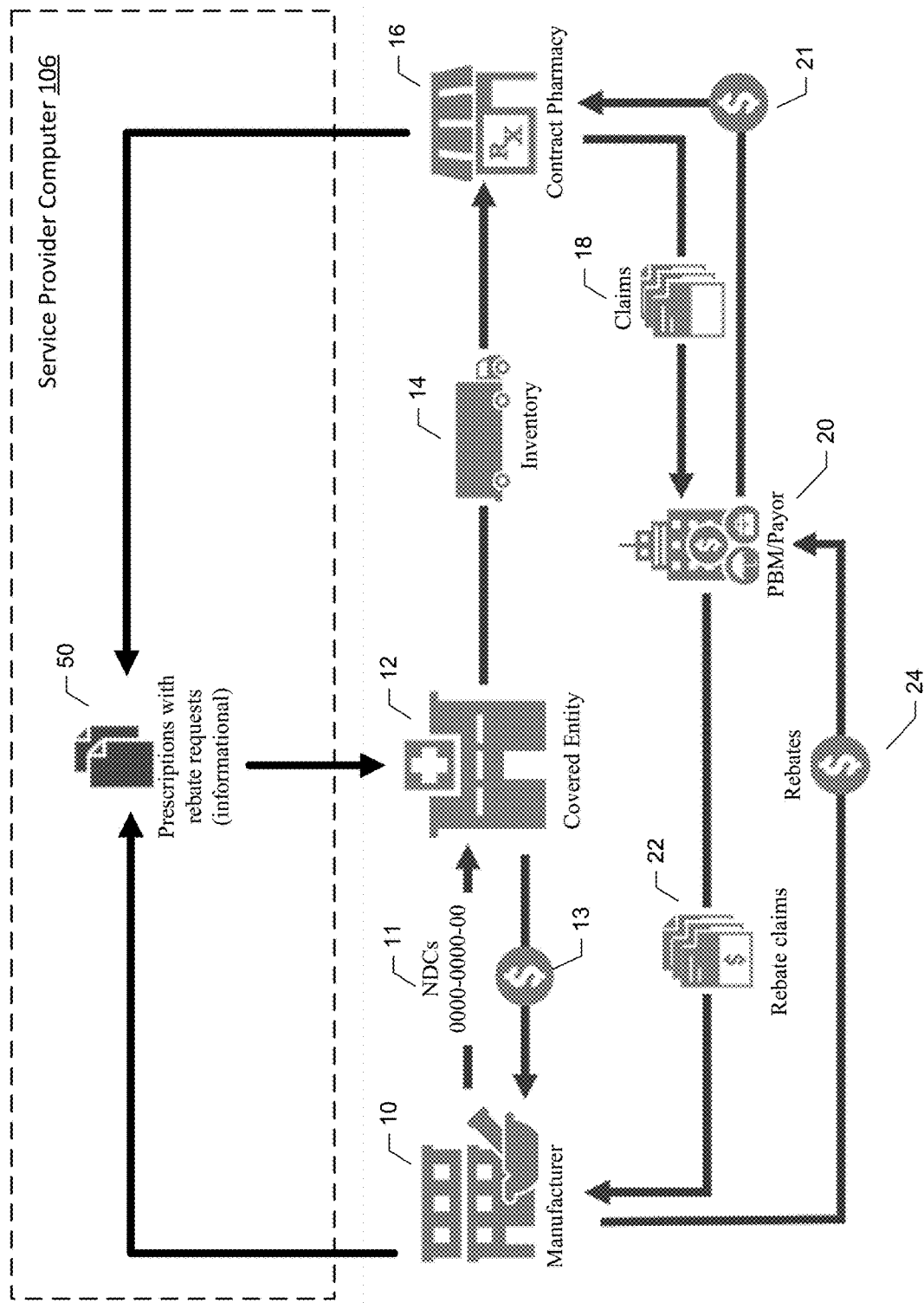

FIG. 1D is an extension of FIG. 1C, and illustrates additional optional operations that may be performed by the service provider computer 106, according to example embodiments. Using the retail data collected from the contract pharmacy 16, and the rebate claims from the manufacturer 10, as described with respect to FIG. 1C, the service provider computer 106 may provide information 50 pertaining to prescriptions having associated rebate requests, to covered entity 12. The reconciled information may be provided to covered entity 12 for informational purposes, and may provide insight regarding non-compliance with the 340B program, such as by the PBM 20 for attempting to obtain rebates on prescriptions filled under the 340B program.

Having introduced some example systems in which example embodiments may operate, FIG. 2A is another overview of an example system that can be used to practice some example embodiments described herein.

The pharmacy computer 104 may be associated with a pharmacy or pharmacy network to facilitate the filling of prescriptions, transmitting prescription claims to a service provider computer 106, and/or the like. For example, the pharmacy computer 104 may be associated with a contract pharmacy, such as contract pharmacy 16, contracted with a covered entity to provide prescription drugs under a discount program, such as the 340B program, or other discounted and/or regulated program. It will be appreciated that in addition to providing prescription medication under the discount program, the pharmacy associated with the pharmacy computer 104 may provide prescription medication to patients via prescription transactions not covered by the 340B program. For example, in one instance, a prescription medication may be provided under the 340B program, and in another instance, the same prescription medication is provided to a patient, but not under the 340B program.

According to certain embodiments, the pharmacy computer 104 may be associated with a national chain pharmacy, local pharmacy chain, individual pharmacy, and/or the like. The pharmacy computer 104 may additionally or alternatively be associated with a physician's office, clinic, long-term care facility, hospital, etc. Accordingly, while the exemplary pharmacy computer 104 may be frequently referenced herein as part of a pharmacy or pharmacy network, the pharmacy computer 104 may be associated with any other healthcare provider, such as a physician's office, hospital and/or other medical facility.

The pharmacy computer 104 may be any processor-driven device that receives prescriptions written and/or submitted by medical practitioners such as but not limited to covered entities. The pharmacy computer 104 may further facilitate the submission of prescription transaction requests made by patients or consumers when obtaining their prescription, and the communication of information associated with prescription transactions to the service provider computer 106. In certain example embodiments, the pharmacy computer 104 may be a point of sale device associated with a pharmacy. The execution of the computer-implemented instructions by the pharmacy computer 104 may form a special purpose computer or other particular machine that is operable to facilitate the submission of pharmacy transaction requests made by patients, pharmacists, and/or the like, and the communication of information associated therewith to a service provider computer 106.

The service provider computer 106 may include, but is not limited to, a processor-driven device that is configured for receiving and processing information from the pharmacy computer 104, PBM computer 108, rebate facilitation computer 110, and/or healthcare entity computer 112, and providing responses and/or information thereto, as described in further detail herein. The service provider computer 106 may provide services relating to the facilitation of healthcare transactions such as but not limited to benefits processing, billing, rebate claim validation, tracking of encounter data, and/or other data and/or the like. In this regard, a healthcare transaction may be referenced herein to include any of the transactions, data, or information transmitted to the service provider computer 106 and processed accordingly. As such, the service provider computer 106 may be operable to facilitate the receipt, routing, and/or processing of healthcare transactions such as prescription transactions, prescription claims, rebate claims, rebate validation requests, and/or associated responses amongst various components and/or subsystems such as, but not limited to, those depicted in FIGS. 1A-1D and FIG. 2A.

In certain exemplary embodiments, the service provider computer 106 may be configured as or may comprise a switch or router that evaluates, modifies, reformats, generates, and/or routes healthcare transactions. For example, the service provider computer 106 may route prescription transactions communicated from the pharmacy computer 104 to a PBM computer 108, such as that associated with a PBM, an insurer, a Medicare or other government healthcare insurance program payer, or other payor. According to certain embodiments, the PBM computer 108 may comprise any other computer system driven by a processor that receives and adjudicates prescription claims on behalf of the payer and/or transmits rebate claims to a rebate facilitation computer 110 associated with a drug manufacturer.

Accordingly, the service provider computer 106 may reformat healthcare transactions into another form of transaction, modify and/or apply edits to the healthcare transaction, and/or modify the recipient information of the reformatted transaction before routing the reformatted, modified and/or edited transaction to another party, (such as PBM computer 108, or other entities depicted in FIGS. 1A-1D and FIG. 2A).

In certain embodiments, the service provider computer 106 may receive rebate claim validation requests from a rebate facilitation computer 110, determine whether an associated prescription claim was made under the 340B program, and provide a rebate claim validation response accordingly. In this regard, the service provider computer 106 may modify the rebate claim validation request with a discount indicator, indicating whether or not a discount was already applied to the associated prescription (by way of 340B pricing, or discount pricing under another regulated and/or discount program).

The rebate facilitation computer 110 may be any processor-driven computing device associated with a prescription drug manufacturer, such as manufacturer 10. The rebate facilitation computer 110 may be configured to receive rebate claims from the PBM computer 108 (associated with PBM 20), and pay or reject the claims accordingly. The rebate facilitation computer 110 may utilize the service provider computer 106 as described in further detail herein, to determine whether the rebate claim should be paid, or if payment of a rebate claim would result in a duplicate discount and should be rejected.

The healthcare entity computer 112 may be any processor-driven computing device associated with a healthcare entity (e.g., provider of healthcare service), such as but not limited to a hospital, physician's office, outpatient office, other medical practice and/or the like. The healthcare entity may include a covered entity such as covered entity 12 (including but not limited to a hospital, clinic and/or the like contracted to provided services aligned with the 340B program or other regulated and/or discount program). In embodiments in which the healthcare entity computer 112 is associated with a covered entity, or covered entity computer, the healthcare entity computer 112 may transmit orders, optionally via the service provider computer 106, for prescription drugs to manufacturer 10, and/or a computer associated therewith, such as but not limited to the rebate facilitation computer 110 or other computing device configured to manage distribution on behalf of the manufacturer 10.). In embodiments in which the healthcare entity computer 112 is associated with a covered entity, or covered entity computer, the healthcare entity computer 112 may be further configured to electronically allocate, optionally via the service provider computer 106, 340B inventory to certain contract pharmacies for dispensing. The healthcare entity computer 112 may be further configured to provide encounter records, or patient encounter data, regarding patient encounters with practitioners of the healthcare service, to the service provider computer 106, enabling the service provider computer 106 to determine if certain prescription claims were associated with the 340B program. In embodiments in which the healthcare entity computer 112 is associated with a covered entity, or covered entity computer, the service provider computer 106 may transmit data, such as information 50 pertaining to prescriptions with rebate requests, to the healthcare entity computer 112.

The eligibility database 114 may comprise any computing device, system, and/or database configured to store and maintain data pertaining to 340B eligibility on behalf of the service provider computer 106. According to certain embodiments, the service provider computer 106 may purchase certain baseline data and/or rules outlining guidelines or rules pertaining to 340B eligibility. For example, the data may comprise correlated diagnoses and prescription drug information that together provide for qualification under 340B. The eligibility database 114 may further comprise a list of entities, or covered entities, covered under the 340B program. The service provider computer 106 may further maintain the eligibility database 114 over time, and as new prescription medication becomes available or become eligible under 340B.

An administrator of the eligibility database 114 and/or service provider computer 106 may further maintain the eligibility database 114 based on their expertise in pharmacy. For example, certain 340B eligibility data may reflect that a certain NDC (National Drug Code) paired with a particular diagnosis(es) or diagnosis code(s) indicates the associated prescription is 340B eligible. However, there may be alternative NDCs and diagnosis pairings which should also be 340B eligible. For example, certain NDCs may have various related NDCs corresponding to the same drug, but having different quantities, days' supply, dosage, and/or the like, that should result in 340B eligibility in certain scenarios. As another example, variations in diagnosis codes may evolve, some of which should have associated 340B eligible prescriptions. In this regard, the administrator may update the eligibility database 114 to reflect additional scenarios and rules to determine 340B eligibility. The eligibility database 114 may therefore provide a foundation for determining eligibility under the 340B program.

Referring now to FIG. 2B, apparatus 200 is a computing device(s) configured for implementing pharmacy computer 104, service provider computer 106, PBM computer 108, rebate facilitation computer 110, healthcare entity computer 112, and/or eligibility database 114, according to example embodiments.

Apparatus 200 may at least partially or wholly embody or be embodied by any of the pharmacy computer 104, service provider computer 106, PBM computer 108, rebate facilitation computer 110, healthcare entity computer 112, and/or eligibility database 114. Apparatus 200 may therefore implement any of the pharmacy computer 104, service provider computer 106, PBM computer 108, rebate facilitation computer 110, healthcare entity computer 112, and/or eligibility database 114, in accordance with some example embodiments, or may be implemented as a distributed system that includes any of the pharmacy computer 104, service provider computer 106, PBM computer 108, rebate facilitation computer 110, healthcare entity computer 112, eligibility database 114, and/or associated network(s).

It should be noted that the components, devices, and elements illustrated in and described with respect to FIG. 2B may not be mandatory and thus some may be omitted in certain embodiments. For example, FIG. 2B illustrates a user interface 216, as described in more detail below, which may be optional in any of the pharmacy computer 104, service provider computer 106, PBM computer 108, rebate facilitation computer 110, and/or healthcare entity computer 112 (such as when a respective computer or server is implemented as a service communicatively connected to a work station or other user device). Additionally, some embodiments may include further or different components, devices, or elements beyond those illustrated in and described with respect to FIG. 2B.

Continuing with FIG. 2B, processing circuitry 210 may be configured to perform actions in accordance with one or more example embodiments disclosed herein. In this regard, the processing circuitry 210 may be configured to perform and/or control performance of one or more functionalities of apparatus 200 in accordance with various example embodiments. The processing circuitry 210 may be configured to perform data processing, application execution, and/or other processing and management services according to one or more example embodiments. In some embodiments apparatus 200, or a portion(s) or component(s) thereof, such as the processing circuitry 210, may be embodied as or comprise a circuit chip. The circuit chip may constitute means for performing one or more operations for providing the functionalities described herein.

In some example embodiments, the processing circuitry 210 may include a processor 212, and in some embodiments, such as that illustrated in FIG. 2, may further include memory 214. The processing circuitry 210 may be in communication with or otherwise control a user interface 216, and/or a communication interface 218. As such, the processing circuitry 210, such as that included in any of the pharmacy computer 104, service provider computer 106, PBM computer 108, rebate facilitation computer 110, healthcare entity computer 112, eligibility database 114, and/or apparatus 200 may be embodied as a circuit chip (e.g., an integrated circuit chip) configured (e.g., with hardware, software, or a combination of hardware and software) to perform operations described herein.

The processor 212 may be embodied in a number of different ways. For example, the processor 212 may be embodied as various processing means such as one or more of a microprocessor or other processing element, a coprocessor, a controller, or various other computing or processing devices including integrated circuits such as, for example, an ASIC (application specific integrated circuit), an FPGA (field programmable gate array), or the like. Although illustrated as a single processor, it will be appreciated that the processor 212 may comprise a plurality of processors. The plurality of processors may be in operative communication with each other and may be collectively configured to perform one or more functionalities of apparatus 200 as described herein. The plurality of processors may be embodied on a single computing device or distributed across a plurality of computing devices collectively configured to function as pharmacy computer 104, service provider computer 106, PBM computer 108, rebate facilitation computer 110, healthcare entity computer 112, eligibility database 114, and/or apparatus 200. In some example embodiments, the processor 212 may be configured to execute instructions stored in the memory 214 or otherwise accessible to the processor 212. As such, whether configured by hardware or by a combination of hardware and software, the processor 212 may represent an entity (e.g., physically embodied in circuitry—in the form of processing circuitry 210) capable of performing operations according to embodiments of the present disclosure while configured accordingly. Thus, for example, when the processor 212 is embodied as an ASIC, FPGA, or the like, the processor 212 may be specifically configured hardware for conducting the operations described herein. Alternatively, as another example, when the processor 212 is embodied as an executor of software instructions, the instructions may specifically configure the processor 212 to perform one or more operations described herein.

In some example embodiments, the memory 214 may include one or more non-transitory memory devices such as, for example, volatile and/or non-volatile memory that may be either fixed or removable. In this regard, the memory 214 may comprise a non-transitory computer-readable storage medium. It will be appreciated that while the memory 214 is illustrated as a single memory, the memory 214 may comprise a plurality of memories. The plurality of memories may be embodied on a single computing device or may be distributed across a plurality of computing devices. The memory 214 may be configured to store information, data, applications, computer program code, instructions and/or the like for enabling apparatus 200 to carry out various functions in accordance with one or more example embodiments. For example, when apparatus 200 is implemented as service provider computer 106, memory 214 may be configured to store computer program code for performing corresponding functions thereof, as described herein according to example embodiments.

Still further, memory 214 may be configured to store routing tables, that facilitate determining the destination of communications received from pharmacy computer 104, PBM computer 108, rebate facilitation computer 110, and/or healthcare entity computer 112. Memory 214 may further include reconciliation tables for tracking the healthcare transactions received from the pharmacy computer 104, PBM computer 108, rebate facilitation computer 110, and/or healthcare entity computer 112, and reconciling them with responses received from any of the aforementioned devices. The memory 214 may further comprise a database, such as eligibility database 114, comprising data and/or rules defining discount program eligibility, such as but not limited to 340B eligibility. Still further, according to certain embodiments, the memory 214 may be modified as described herein, to reformat healthcare transactions with additional information received, determined and/or generated according to example embodiments.

The memory 214 may be further configured to buffer input data for processing by the processor 212. Additionally or alternatively, the memory 214 may be configured to store instructions for execution by the processor 212. In some embodiments, the memory 214 may include one or more databases that may store a variety of files, content, or data sets. Among the contents of the memory 214, applications may be stored for execution by the processor 212 to carry out the functionality associated with each respective application. In some cases, the memory 214 may be in communication with one or more of the processor 212, user interface 216, and/or communication interface 218, for passing information among components of apparatus 200.

The optional user interface 216 may be in communication with the processing circuitry 210 to receive an indication of a user input at the user interface 216 and/or to provide an audible, visual, mechanical, or other output to the user. As such, the user interface 216 may include, for example, a keyboard, a mouse, a display, a touch screen display, a microphone, a speaker, and/or other input/output mechanisms. As such, in embodiments in which apparatus 200 is implemented as the rebate facilitation computer 110 and/or PBM computer 108, the user interface 216 may, in some example embodiments, provide means for displaying information regarding the rebate claim validation. For example, the user interface 216 may display a message that a certain prescription is not valid for an inventive and/or rebate because it was filled under a discount program such as 340B. In some example embodiments, aspects of user interface 216 may be limited or the user interface 216 may not be present.

The communication interface 218 may include one or more interface mechanisms for enabling communication with other devices and/or networks. In some cases, the communication interface 218 may be any means such as a device or circuitry embodied in either hardware, or a combination of hardware and software that is configured to receive and/or transmit data from/to a network and/or any other device or module in communication with the processing circuitry 210. By way of example, the communication interface 218 may be configured to enable communication amongst any of pharmacy computer 104, PBM computer 108, rebate facilitation computer 110, and/or healthcare entity computer 112, and/or apparatus 200 over a network. Accordingly, the communication interface 218 may, for example, include supporting hardware and/or software for enabling wireless and/or wireline communications via cable, digital subscriber line (DSL), universal serial bus (USB), Ethernet, or other methods.

A network, such as the network in which any of the systems of FIG. 1A, 1B, 1C, 1D, or 2A or components thereof or components described herein may operate, (e.g., pharmacy computer 104, PBM computer 108, rebate facilitation computer 110, healthcare entity computer 112, apparatus 200, and/or the like) may include a local area network, the Internet, any other form of a network, or any combination thereof, including proprietary private and semi-private networks and public networks. The network may comprise a wired network and/or a wireless network (e.g., a cellular network, wireless local area network, wireless wide area network, some combination thereof, and/or the like).

Having now described an example apparatus for implementing example embodiments, FIG. 3 is a flowchart illustrating example operations of an apparatus 200, according to some example embodiments. The operations of FIG. 3 may be performed by apparatus 200, such as with the service provider computer 106, and/or the like.

As shown by operation 302, apparatus 200 may include means, such as processor 212, memory 214, communication interface 218, and/or the like, for receiving an indication of a rebate claim validation request from a rebate facilitation computer. For example, as illustrated in FIG. 4, a rebate claims feed 400 flows from the rebate facilitation computer 110 to the service provider computer 106. In certain embodiments, the rebate claim validation requests may be forwarded and/or transmitted to the service provider computer 106 from rebate facilitation computer 110 as rebate claims are received from the PBM computer 108. In some embodiments, the rebate claims may be transmitted to the service provider computer 106 in a batch process, and/or the like.

In certain embodiments, a rebate claim validation request may comprise requestor-provided prescription drug information, such as but not limited to a manufacturer (MFG) NDC, MFG Rx # (e.g., prescription number), MFG quantity (QTY), MFG date, MFG Pharmacy National Provider Identifier (NPI), and/or the like. The term "requestor-provided," and the prefix "MFG" are used to indicate the fields come from the rebate facilitation computer 110 and/or associated manufacturer. The fields listed above and in FIG. 4 are provided merely as an example, and it will be appreciated that additional or alternative fields may be included in a rebate claim validation request. For example, another format of pharmacy identifier may be used instead of or in addition to NPI. It should further be appreciated that in certain embodiments, the rebate facilitation computer 110 and/or manufacturer 10, may not have access to patient information associated with the rebate claim, and/or encounter records associated with the rebate claim, and such data may be absent from, or not included in a rebate claim validation request.

Returning to FIG. 3, in operation 304, apparatus 200 may include means, such as processor 212, memory 214, communication interface 218, and/or the like, for receiving an indication of a plurality of adjudicated prescription claims received from a plurality of pharmacy computers 104. For example, see the adjudicated scripts feed 410 of FIG. 4. In this regard, a contract pharmacy such as that associated with pharmacy computer 104 may provide the adjudicated prescription claims to the service provider computer 106 to comply with certain requirements of a program such as the 340B program.

In certain embodiments, an adjudicated prescription claim comprises, among other fields, pharmacy-provided prescription drug information and patient information associated with a patient with whom a respective adjudicated prescription claim is associated. For example, as illustrated in FIG. 4, an adjudication prescription claim in the data feed 410, transmitted from the pharmacy computer 104 to the service provider computer 106 may include NDC, Rx #, quantity (QTY), date, pharmacy NPI, patient information, and/or the like. The term "pharmacy-provided" is used to indicate the particular instances of data are received from the pharmacy computer 104. The patient information may comprise a plurality of data such as but not limited to name, date of birth, address, and/or the like. It will be appreciated that any number of fields may be included into the patient info, such as those utilized in patient matching algorithms and/or the like. The adjudicated script feed 410 may be provided on an on-going basis, as the pharmacy computer 104 receives adjudicated responses from a PBM computer 108, for example. The adjudicated prescription claims may be alternatively or additionally transmitted via batch processing, such as via processes occurring nightly.

Returning to FIG. 3, in operation 306, apparatus 200 may include means, such as processor 212, memory 214, communication interface 218, and/or the like, for determining a corresponding adjudicated prescription claim that corresponds with the rebate claim validation request. In this regard, the rebate claim validation request referenced in operation 302 may be compared against any of the adjudication prescription claims referenced in operation 304. It will be appreciated that numerous processes and/or rules may be utilized to determine a corresponding adjudicated prescription claim from the plurality of adjudicated prescription claims. For example, certain embodiments, such as with processor 212, may compare one or more of the requestor-provided prescription drug information to one or more pharmacy-provided prescription drug information of adjudicated prescription claims until a match is identified. For example, the Rx #, which may be generated by a pharmacy computer 104 such that an Rx # is unique to a particular prescription claim, may be matched in a rebate claim validation request to an adjudicated prescription claim.

As shown in operation 308, although not performed in any specific order, and optionally performed on an ongoing or continual basis, apparatus 200 may include means, such as processor 212, memory 214, communication interface 218, and/or the like, for receiving an indication of a plurality of encounter records received from a covered entity computer. As shown in FIG. 4, a data feed of encounter records 420, may be transmitted from the healthcare entity computer 112 to service provider computer 106. The encounter records may be transmitted by the healthcare entity computer 112 to the service provider computer 106, for a variety of purposes, such as but not limited to compliance by the covered entity with a program, such as the 340B program. As another example, the encounter records may be provided for other purposes, such as but not limited to insurance claim processing and/or adjudication, and/or the like.

In certain embodiments, the encounter records may be provided via a HL7 (Health Level 7) feed, such as the admit, discharge, transfer (ADT) data feed.

An encounter record may reflect data captured by a physician or other staff of the covered entity during a patient's appointment for healthcare service. An encounter record may include an eRX, (electronic prescription) such as a prescription transmitted electronically to a pharmacy computer 104. The eRX may therefore include the NPI identifying the pharmacy to which the prescription was transmitted. Accordingly, an encounter record may include any prescription drug information, such as, but not limited to NDC, or other medication identifier of a prescribed medication. An encounter record may further include any number of diagnoses or diagnosis codes, patient info and/or the like. It will be appreciated that in certain embodiments, the data feed 420 may include encounter data from healthcare entity computers 112 that are not covered entities under the discount program, such as the 340B program. In this regard, it may not be readily apparent from an encounter record alone, whether an associated prescription or encounter is associated with a covered entity and/or discount program, such as the 340B program.

It will be appreciated that similar to the data feeds 400 and 410, the data feed of encounter records may be provided on a continual or ongoing basis. For example, the healthcare entity computer 112 may transmit encounter records to the service provider computer 106 as the respective patient encounters are completed, or as apart of a batch process occurring nightly, for example.

Returning to FIG. 3, in operation 310, apparatus 200 may include means, such as processor 212, memory 214, communication interface 218, and/or the like, for generating, by at least accessing the plurality of encounter records, a discount indicator indicating whether the corresponding adjudicated prescription claim (and therefore the rebate claim validation request) is associated with a discount program, such as the 340B program. Operation 310 is described in further detail below with reference to FIG. 5. The discount indicator may be a Yes/No flag or Boolean value, for example, and may be included in a response to the rebate facilitation computer 110.

Accordingly, in operation 312, apparatus 200 may include means, such as processor 212, memory 214, communication interface 218, and/or the like, for causing transmission of a rebate claim validation response to the rebate facilitation computer 110, the rebate claim validation response comprising the discount indicator and information associating the rebate claim validation response to the rebate claim validation request. For example, in FIG. 4, the response claims feed 430 transmits rebate claim validation responses to the rebate facilitation computer 110. A rebate claim validation response may include any information associating the response to the rebate claim validation request previously transmitted by rebate facilitation computer 110 and received by service provider computer 106 with respect to operation 302, such as, but not limited to, MFG NDC, MFG Rx #, MFG QTY, MFG Date, and/or MFG pharmacy NPI. The response may further include the discount indicator, such as a 340B indicator determined in operation 310.

Accordingly, the rebate facilitation computer 110 may receive the rebate claim validation response, and provide a response to the PBM computer 108 to either honor or reject a rebate claim, based on the discount indicator and/or 340B indicator. For example, a discount indicator, or 340B indicator set to "Yes" may indicate the prescription is attributed to a 340B discounted prescription, and the manufacturer and/or rebate facilitation computer 110 may not be obligated to honor a rebate and/or incentive. If the discount indicator, or 340B indicator is set to "No," assuming other requirements, such as may be enforced by the rebate facilitation computer 110, are met, the manufacturer may be obligated via a contract with the PBM to honor the rebate and/or incentive.

Based on the discount indicator, in certain embodiments, the rebate facilitation computer 110 may systematically or automatically accept or reject the rebate claim submitted by the PBM computer 108. A systematic or automatic rejection may be considered a corrective action to reduce or prevent duplicate discounts. Without the advantages of example embodiments, the rebate facilitation computer 110 may otherwise pay, or accept, rebate claims that should have been rejected based on eligibility under a discount program, such as the 340B program.

In certain example embodiments, the service provider computer 106 may be further configured to direct a user interface 216 of the rebate facilitation computer 110 to display a message including the discount indicator, and/or corresponding details indicating determined qualification in a discount program, or non-qualification in the discount program. As another example, the service provider computer 106 may be further configured to direct a user interface 216 of the PBM computer 108 to display a similar message, such as one indicating a rebate claim is rejected or accepted due to determined qualification in a discount program, or non-qualification in the discount program. In certain embodiments, a report may be generated including a listing of rebate claims that were rejected.

In operation 314, apparatus 200 may include means, such as processor 212, memory 214, communication interface 218, and/or the like, for causing transmission of information relating to the rebate claim validation request to a covered entity computer, such as a healthcare entity computer 112 identified as being associated with a covered entity, and in some embodiments, identified as the covered entity associated with the particular rebate claim validation request. Accordingly, information regarding 340B prescription transactions originating from a particular covered entity, which result in a rebate claim being made by the PBM, may be provided to the covered entity so the covered entity is aware of PBMs that submitted rebate claims.

A shown in FIG. 440, a rebate request feed may be transmitted from the service provider computer 106 to the healthcare entity computer 112. The information relating to the rebate claim validation request may indicate to the covered entity which prescriptions resulted in the PBM computer 108 submitting a rebate claim. Accordingly, the healthcare entity computer 112 may utilize the information to ensure compliance of the 340B prescriptions originating from the covered entity, particularly with regard to downstream processing and rebate claims relating to the prescriptions. For example, in health systems that have a health-sponsored plan, agreements may contain language burdening the health system with the prevention of duplicate discounts through identification of individual claims to be marked as ineligible for rebates. Without the advantages of example embodiments, the covered entity may have no visibility into which prescriptions are actually requested as rebate claims. Providing the information relating to rebate claim validation requests to the covered entity computer, such as healthcare entity computer 112, may allow the covered entity to audit their 340B processes. Additionally, covered entities may be made aware of Medicaid and other type claims that are being requested, but should not be eligible for rebates, and proactively take corrective action to prevent those claims from reaching the manufacturer.

According to certain embodiments, the service provider computer 106 may be configured to direct output on a display of healthcare entity computer 112, such as user interface 216, providing the information relating to the rebate claim validation requests.

As introduced above, in operation 310, example embodiments, such as the service provider computer 106 may generate a discount indicator by accessing encounter records provided by the healthcare entity computer 112. FIG. 5 provides additional detail on generating the discount indicator, according to certain example embodiments. As set forth above with respect to operation 306, example embodiments may determine a corresponding adjudicated prescription claim that corresponds with the rebate claim validation request. Example embodiments may then utilize the information from the adjudicated prescription claim, compare it to encounter records, and determine whether there is a corresponding encounter record indicating eligibility under the discount program, such as the 340B program.

In operation 500 of FIG. 5, apparatus 200 may include means such as processor 212, memory 214, communication interface 218, and/or the like, for accessing an eligibility database, such as eligibility database 114, configured to maintain records comprising associations amongst diagnoses, prescription drug information, and eligibility in a discount program, such as the 340B program, and/or a listing of covered entities under the discount program. The information stored in the eligibility database 114 may be utilized in additional operations in FIG. 5, described in further detail below.

In operation 504, apparatus 200 may include means, such as processor 212, memory 214, communication interface 218, and/or the like, for determining whether there are one or more encounter records, from the plurality of encounter records, relevant to the corresponding adjudicated prescription claim. To make such a determination, apparatus 200 may include means, such as processor 212, memory 214, communication interface 218, and/or the like, for determining whether there are one or more relevant encounter records from the plurality of encounter records that (1) comprise patient information associated with the patient information of the corresponding adjudicated prescription claim, and (2) comprise prescription drug information consistent with the pharmacy-provided prescription drug information of the corresponding adjudicated prescription claim. In this regard, example embodiments may identify one or more encounter records that may be relevant to the corresponding adjudication prescription claim (and therefore the rebate claim validation request). Example embodiments may therefore identify relevant encounter records, or potentially matching encounter records to the adjudicated prescription claim by identifying matching, or corresponding patient information and/or prescription drug information. Similar to as described above, any algorithms, processes, and data points related to patient information may be utilized to perform patient matching. And, in certain embodiments, various processes, algorithms, and/or datasets such as those associated with the eligibility database 114 may be utilized to determine whether prescription drug information from an encounter record is consistent with the pharmacy-provided prescription drug information of the corresponding adjudicated prescription claim. The phrase "is consistent with" is used to clarify that the prescription drug information may not necessarily include exact matches nor one-to-one matches of certain data fields, but may rather indicate prescription drug information from the encounter data that indicates eligibility in a discount program such as the 340B program, corresponding to pharmacy-provided prescription drug information which also indicates eligibility under the discount program based on related rules and/or datasets. For example, as described above, the eligibility database 114 may be configured to correlate various NDCs having the same associated prescription drug, but merely in different quantities, days' supply, and/or dosages, for example. However, in certain scenarios, a matching NDC may indeed indicate the prescription drug information from an encounter record is consistent with the pharmacy-provided prescription drug information.

In any event, if there are no relevant encounter records indicating (1) patient information associated with the patient information of the corresponding adjudicated prescription claim, and (2) prescription drug information consistent with the pharmacy-provided prescription drug information of the corresponding adjudicated prescription claim, example embodiments may determine or generate, at operation 510, the discount indicator as "No." For example, in an instance it is determined there are no relevant encounter records from the plurality of encounter records that comprise patient information associated with the patient information of the corresponding adjudicated prescription claim, and comprise prescription drug information consistent with the pharmacy-provided prescription drug information of the corresponding adjudicated prescription claim, apparatus 200 may include means, such as processor 212, memory 214, communication interface 218, and/or the like, for, generating the discount indicator to indicate the corresponding adjudicated prescription claim is not associated with a discount program.

If example embodiments determine there is at least one relevant encounter record (comprising (1) patient information associated with the patient information of the corresponding adjudicated prescription claim, and (2) prescription drug information consistent with the pharmacy-provided prescription drug information of the corresponding adjudicated prescription claim), processing may continue to operation 516.

In operation 516, having identified at least one relevant encounter record in which the patient information matches that of the corresponding adjudicated prescription claim, and further includes prescription drug information consistent with the pharmacy-provided prescription drug information, apparatus 200 may include means, such as processor 212, memory 214, communication interface 218, and/or the like, for determining whether one or more encounter records relevant to the corresponding adjudicated prescription claims are associated with a covered entity. In this regard, example embodiments may determine, whether the healthcare entity computer 112 from which an encounter record is received, is from a covered entity computer associated with a covered entity. For example, an encounter record may have an identifier appended thereto, indicating the source from which it originated, such as an identifier of a healthcare entity computer 112. Example embodiments may access a list or database, such as eligibility database 114, to determine whether the healthcare entity computer 112 is a covered entity computer, or associated with a covered entity. If so, example embodiments may determine the encounter record is associated with a covered entity and processing may continue to operation 520.

In some instances, determining whether the encounter record came from a cover entity computer may not be easily discernable, and example embodiments may utilize other information to make such a determination. For example, an eRX and/or encounter record may not include an indication of a covered entity, but otherwise may include a prescriber identifier. Example embodiments may access a list or database of prescribers who are authorized to write 340B prescriptions. If the encounter record and/or eRX is associated with a prescriber authorized to write 340B prescriptions, example embodiments may further determine, by accessing eligibility database 114, if the prescriber works at the associated covered entity full-time or part-time. If the prescriber works at a covered entity full-time, example embodiments may determine the one or more encounter records (e.g., the encounter record(s) relevant to the corresponding adjudicated prescription claims are associated with a covered entity, and processing may continue to operation 520.

If none of the encounter records are associated with a covered entity, example embodiments may determine that the prescription transaction is not eligible under the discount program, such as the 340B program, and the discount indicator may be set to "No" (510).

In operation 520, having identified at least one relevant encounter record in which the patient information matches that of the corresponding adjudicated prescription claim and includes prescription drug information consistent with the pharmacy-provided prescription drug information (504), and that is associated with a covered entity (516), apparatus 200 may include means, such as processor 212, memory 214, communication interface 218, and/or the like, for determining whether any of the one or more relevant encounter records comprise prescription drug information and diagnosis information indicating eligibility under the discount program, such as the 340B program. As set forth above, eligibility rules to qualify prescription transactions under certain programs such as the 340B program may be complex, and may require certain groupings of prescription drug information, diagnosis(es) (such as diagnosis code(s)), and/or the like) that qualify the prescription transaction for discount pricing, or 340B pricing. The associations amongst diagnoses, prescription drug information, and eligibility e.g., (Yes or No) in a discount program provided by the eligibility database 114 may therefore be utilized to determine whether any of the relevant encounter records (identified in operation 504) indicate qualification under the program, such as 340B.

For example, if executing of any one rule, or more than one rule, configured in the eligibility database 114 indicates program eligibility, the determination may indicate to example embodiments, such as the service provider computer 106, of an eligible prescription transaction under the program, such as the 340B program, and the discount indicator may be set to "Yes" (530). If the execution of all applicable rules (applicable rules as indicated by the eligibility database 114) yield no results of eligibility, example embodiments may determine that the prescription transaction is not eligible under the discount program, such as the 340B program, and the discount indicator may be set to "No" (510).

As yet another example, certain discount program rule configurations may require a plurality of applicable rules to be satisfied to qualify under the program. In such examples, the eligibility database 114 may indicate the plurality of rules required to be satisfied for a certain scenario, and in such instances, example embodiments may validate all applicable rules, and may only proceed to operation 530, setting of the discount indicator to "Yes" if all applicable and required rules are satisfied. If there are a plurality of applicable rules required to be validated, and one or more are not satisfied, example embodiments may set the discount indicator to "No" (510).

It will be appreciated that in certain embodiments, the encounter data may comprise eRX data, and the eRX data may be the only encounter data needed to determine eligibility, when compared to the results in the eligibility database. For example, example embodiments may identify a covered entity from which an eRX originated and may further identify prescription drug information of the drug prescribed. The eRX may further include the patient information, enabling example embodiments to match the eRX to the patient identified in the rebate claim validation request. It will be appreciated that while described herein as "encounter data," in certain embodiments, the eRX data may be provided via a separate data feed from other encounter data such as those relating to details of a patient-physician encounter.

In certain embodiments, the eRX data may not be available. As such, as described with respect to operation 520, certain encounter records may be more complex than others to determine whether the prescription transaction is eligible under the discount program. For example, certain encounter data may not clearly indicate a covered entity from which the prescription was prescribed, but may include a prescriber and/or physician identifier. In this regard, example embodiments may access Accordingly, the discount indicator referenced in operation 310 may be generated, or set, as described above with respect to FIG. 5, and returned to the rebate facilitation computer 110 as described with reference to operation 312.

In certain example embodiments, some variations of the operation of FIG. 5 may be provided. For example, several operations of FIG. 5, such as 504, 516, and/or 520 may be considered a series of example filters, conditions, or rules to apply to encounter records to determine if one or more indicate eligibility in a discount program, such as the 340B program. Accordingly, it will be appreciated that the filters, conditions or rules, may be performed and/or executed in any order.

As another example to a variation of operations of FIG. 5, it will be appreciated that the service provider computer 106 may not necessarily reach a definitive response to execution of any of operations 504, 516, and/or 520. Accordingly, in response to execution of various rules, conditions, or filters, as described with respect to FIG. 5, in addition to a discount indicator, a confidence level may be generated, indicating a confidence level of the service provider 106 of being accurate in its determination of the discount indicator. For example, service provider 106 may calculate a confidence level based on a percentage or ratio of rules validated and satisfied. In certain embodiments, if a confidence level falls below a specified or predefined confidence interval, the discount indicator may not be provided to the rebate facilitation computer 110, and/or example embodiments may trigger manual review and validation. According to certain embodiments, certain information described above, utilized in the process for determining whether a rebate claim is associated with a discount program, such as 340B, may be redacted from certain records, or missing. Example embodiments may therefore make inferences or access other data points to make such inferences and alter the confidence level accordingly. Accordingly, conditions labeled as "Yes" in the flowchart of FIG. 5 may be considered satisfied when a certain predefined threshold of confidence is achieved for the certain condition, such as, for example 80%.

Numerous technical advantages may be provided according to the example embodiments provided herein. The generation of the discount indicator may provide a meaningful limitation that enables the manufacturer and/or rebate facilitation computer 110 to take corrective action and appropriately reject certain rebate claims that were already subject to a discount, such as under the 340B program. Example embodiments therefore enable the corrective action of reducing or preventing duplicate discounts. Example embodiments further enable the covered entity, such as covered entity 12 to take corrective action in enforcing certain discount program parameters and/or processes, and therefore reduce or prevent non-compliant rebate claims (claims associated with the discount program) from being made by PBMs).

Moreover, according to certain embodiments, the service provider computer 106 may function to perform compliance-related services, such as those required by a discount program such as the 340B program, on behalf of a covered entity, contract pharmacy, and/or the like. The service provider computer 106 may also function to provide other healthcare related technology and data-related services relating to claims processing, payment, and/or adjudication. In this regard, the service provider computer 106 may be pre-configured to receive any or both of the data feeds 410 and 420, relating to respective adjudicated prescription claims and encounter records. As such, the service provider computer 106 may be improved to provide the additional rebate claim validation functionality to the rebate facilitation computer 110, without requiring additional overhead, in terms of processing and memory resources that may otherwise be expended to retrieve such data from the pharmacy computer 104 and/or healthcare entity computer 112. Similarly, the pharmacy computer 104 and/or healthcare entity computer 112 may conserve processing and memory resources that may otherwise be expended in answering such requests for prescription claims and encounter records from a service provider computer 106 and/or other computer. Accordingly, the service provider computer 106, pharmacy computer 104 and/or healthcare entity computer 112 may conserve processing resources and memory resources associated with the routing of such requests and responses otherwise needed to respond to such requests. In this regard, leveraging the data feeds 410 and 420 provides an improvement to the service provider computer 106, and further conserves processing resources and memory resources that may otherwise need to be expended to provide for rebate claim validation.

Moreover, example embodiments provide improvements to the technology of rebate claims processing and/or rebate facilitation computers 110. Without the advantages of the example embodiments provided herein, many rebate facilitation computers 110 may automatically process rebate claims transmitted by the PBM computer 108, providing no reconciliation or validation. Such rebate facilitation computers 110 and/or associated rebate claims processing technology may therefore otherwise suffer from incorrectly paying rebates and/or incentives that should not be paid, and therefore potentially violate certain program regulations such as 340B regulations. Enabling the rebate claims processing technology and/or rebate facilitation computers 110 to discern between valid claims and invalid claims according to associated eligibility under a discount program, as provided according to example embodiments, provides an improvement to the technology of rebate claims processing, and an improvement to the rebate facilitation computers 110.

As yet another example, example embodiments may provide the rebate claims validation services while utilizing fewer processing resources and memory resources in comparison to other methods. For instance, some third parties may attempt to provide rebate claim validation by consulting with the covered entity on a case-by-case basis. A covered entity 110 may therefore need to expend considerable resources to process each request made by the third party and provide a response. In some instances, administrators or staff of the covered entity may be requested to login to a website of the third party to individually process and respond to individual rebate claim validation requests. Hosting and maintaining such a website or service may utilize additional processing resources and memory resources, and may further utilize network resources to enable communication via the website. In contrast, example embodiments utilize the data feed 420 provided by the healthcare entity computer 112 to generate the discount indicator and provide the rebate claim validation service, thereby enabling the covered entity 112 to conserve resources otherwise expended to answer requests from third parties, and enabling such providers and associated networks to conserve processing, memory and network resources otherwise expended to host and maintain websites, and facilitate related communications.

Other implementations providing rebate claim validation services may rely on purchasing data, and may therefore introduce security risks to patient data, and the providers of such data, such as the pharmacy computer 104 and/or covered entity 112. The pharmacy computer 104 and/or covered entity 112 may therefore benefit from the technical improvements provided by example embodiments, by enabling the service provider computer 106 to leverage the existing data feeds 410 and/or 420, thereby eliminating or reducing the need for pharmacies and/or covered entity to provide and/or sell data to additional third parties who in may in turn sell the data or use it to perform rebate claim validation services. The example embodiments provided herein therefore enable the pharmacy computer 104 and/or covered entity 112 to stop or decrease the provision of data to certain third parties, thereby reducing related security and privacy vulnerabilities, and improving the technology of the pharmacy computer 104 and/or covered entity 112.

It will be appreciated that the figures are each provided as examples and should not be construed to narrow the scope or spirit of the disclosure in any way. In this regard, the scope of the disclosure encompasses many potential embodiments in addition to those illustrated and described herein. Numerous other configurations may also be used to implement embodiments of the present invention.

FIGS. 3 and 5 illustrate operations of a method, apparatus, and computer program product according to some example embodiments. It will be understood that each operation of the flowchart or diagrams, and combinations of operations in the flowchart or diagrams, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may comprise one or more memory devices of a computing device (for example, memory 214) storing instructions executable by a processor in the computing device (for example, by processor 212). In some example embodiments, the computer program instructions of the computer program product(s) which embody the procedures described above may be stored by memory devices of a plurality of computing devices. As will be appreciated, any such computer program product may be loaded onto a computer or other programmable apparatus (for example, apparatus 200) to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product may comprise an article of manufacture which implements the function specified in the flowchart block(s). The computer program instructions of one or more computer program products may also be loaded onto a computer or other programmable apparatus (for example, apparatus 200 and/or other apparatus) to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. An apparatus comprising at least one processor and at least one memory including computer program code, the at least one memory and the computer program code configured to, with the processor, cause the apparatus to at least:
   receive an indication of a rebate claim validation request from a rebate facilitation computer associated with a prescription drug manufacturer, the rebate claim validation request comprising requestor-provided prescription drug information;
   receive an indication of a plurality of adjudicated prescription claims received from a plurality of pharmacy computers, wherein an adjudicated prescription claim comprises pharmacy-provided prescription drug information and patient information associated with a patient with whom a respective adjudicated prescription claim is associated;
   determine a corresponding adjudicated prescription claim that corresponds with the rebate claim validation request, from the plurality of adjudicated prescription claims, by matching one or more of the requestor-provided prescription drug information to one or more pharmacy-provided prescription drug information;
   receive a plurality of encounter records from a healthcare entity computer, an encounter record comprising a medication identifier of a prescribed medication, diagnosis information, and patient information;
   generate, by at least accessing the plurality of encounter records received from the healthcare entity computer, and the corresponding adjudication prescription claim received from a prescription claim computer, a discount indicator indicating whether the corresponding adjudicated prescription claim is associated with a discount program; and cause transmission of a rebate claim validation response to the rebate facilitation computer, the rebate claim validation response comprising the discount indicator and information associating the rebate claim validation response to the rebate claim validation request, wherein in an instance the discount indicator indicates a discount was applied, an associated rebate request received from a prescription benefits manager (PBM) computer is automatically rejected by the rebate facilitation computer associated with the prescription drug manufacturer.

2. The apparatus of claim 1, wherein the discount program is the 340B program, and the discount indicator indicates whether or not the corresponding adjudicated prescription claim reflects 340B pricing under the 340B program.

3. The apparatus according to claim 1, wherein generating the discount indicator comprises:
determining whether there are one or more relevant encounter records from the plurality of encounter records that comprise patient information associated with the patient information of the corresponding adjudicated prescription claim, and comprise prescription drug information consistent with the pharmacy-provided prescription drug information of the corresponding adjudicated prescription claim; and
in an instance it is determined there are no relevant encounter records from the plurality of encounter records that comprise patient information associated with the patient information of the corresponding adjudicated prescription claim, and comprise prescription drug information consistent with the pharmacy-provided prescription drug information of the corresponding adjudicated prescription claim, generating the discount indicator to indicate the corresponding adjudicated prescription claim is not associated with a discount program.

4. The apparatus according to claim 3, wherein in an instance it is determined there are one or more relevant encounter records from the plurality of encounter records that comprise patient information associated with the patient information of the corresponding adjudicated prescription claim, generating the discount indicator further comprises:
accessing an eligibility database configured to maintain records comprising associations amongst diagnoses, prescription drug information, and eligibility in a discount program;
based on the associations amongst diagnoses, prescription drug information, and discount program eligibility, determine whether any of the one or more relevant encounter records are associated with a covered entity and comprise prescription drug information and diagnosis information indicating eligibility under the discount program;
in an instance one or more of the one or more relevant encounter records are associated with the covered entity comprise prescription drug information and diagnosis information indicating eligibility under the discount program, generating the discount indicator to indicate the corresponding adjudicated prescription claim is associated with a discount program; and
in an instance none of the one or more relevant encounter records are associated with the covered entity comprise prescription drug information and diagnosis information indicating eligibility under the discount program, generating the discount indicator to indicate the corresponding adjudicated prescription claim is not associated with a discount program.

5. The apparatus according to claim 4, wherein determining whether any of the one or more relevant encounter records are associated with a covered entity comprises determining whether the healthcare entity computer from which the one or more relevant encounter records originated are associated with the covered entity.

6. The apparatus according to claim 4, wherein determining whether any of the one or more relevant encounter records are associated with a covered entity comprises determining whether a prescriber associated with the one or more relevant encounter records is associated with the covered entity.

7. The apparatus according to claim 1, wherein the at least one memory and the computer program code are further configured to, with the processor, cause the apparatus to at least:
cause transmission of information relating to the rebate claim validation request to a covered entity computer.

8. A method comprising:
receiving an indication of a rebate claim validation request from a rebate facilitation computer associated with a prescription drug manufacturer, the rebate claim validation request comprising requestor-provided prescription drug information;
receiving an indication of a plurality of adjudicated prescription claims received from a plurality of pharmacy computers, wherein an adjudicated prescription claim comprises pharmacy-provided prescription drug information and patient information associated with a patient with whom a respective adjudicated prescription claim is associated;
determining a corresponding adjudicated prescription claim that corresponds with the rebate claim validation request, from the plurality of adjudicated prescription claims, by matching one or more of the requestor-provided prescription drug information to one or more pharmacy-provided prescription drug information;
receiving a plurality of encounter records from a healthcare entity computer, an encounter record comprising a medication identifier of a prescribed medication, diagnosis information, and patient information;
generating, by at least accessing the plurality of encounter records received from the healthcare entity computer, and the corresponding adjudication prescription claim received from a prescription claim computer, a discount indicator indicating whether the corresponding adjudicated prescription claim is associated with a discount program; and
causing transmission of a rebate claim validation response to the rebate facilitation computer, the rebate claim validation response comprising the discount indicator and information associating the rebate claim validation response to the rebate claim validation request, wherein in an instance the discount indicator indicates a discount was applied, an associated rebate request received from a prescription benefits manager (PBM) computer is automatically rejected by the rebate facilitation computer associated with the prescription drug manufacturer.

9. The method of claim 8, wherein the discount program is the 340B program, and the discount indicator indicates whether or not the corresponding adjudicated prescription claim reflects 340B pricing under the 340B program.

10. The method of claim 8, wherein generating the discount indicator comprises:
determining whether there are one or more relevant encounter records from the plurality of encounter records that comprise patient information associated with the patient information of the corresponding adjudicated prescription claim, and comprise prescription drug information consistent with the pharmacy-provided prescription drug information of the corresponding adjudicated prescription claim; and in an instance it is determined there are no relevant encounter records from the plurality of encounter records that comprise patient information associated with the patient information of the corresponding adjudicated prescription claim, and comprise prescription drug information consistent with the pharmacy-provided prescription drug information of the corresponding adjudicated prescription claim, generating the discount indicator to indicate the corresponding adjudicated prescription claim is not associated with a discount program.

11. The method of claim 10, wherein in an instance it is determined there are one or more relevant encounter records from the plurality of encounter records that comprise patient information associated with the patient information of the corresponding adjudicated prescription claim, generating the discount indicator further comprises:

accessing an eligibility database configured to maintain records comprising associations amongst diagnoses, prescription drug information, and eligibility in a discount program;

based on the associations amongst diagnoses, prescription drug information, and discount program eligibility, determine whether any of the one or more relevant encounter records are associated with a covered entity and comprise prescription drug information and diagnosis information indicating eligibility under the discount program;

in an instance one or more of the one or more relevant encounter records are associated with the covered entity comprise prescription drug information and diagnosis information indicating eligibility under the discount program, generating the discount indicator to indicate the corresponding adjudicated prescription claim is associated with a discount program; and in an instance none of the one or more relevant encounter records are associated with the covered entity comprise prescription drug information and diagnosis information indicating eligibility under the discount program, generating the discount indicator to indicate the corresponding adjudicated prescription claim is not associated with a discount program.

12. The method of claim 11, wherein determining whether any of the one or more relevant encounter records are associated with a covered entity comprises determining whether the healthcare entity computer from which the one or more relevant encounter records originated are associated with the covered entity.

13. The method of claim 11, wherein determining whether any of the one or more relevant encounter records are associated with a covered entity comprises determining whether a prescriber associated with the one or more relevant encounter records is associated with the covered entity.

14. The method of claim 8, further comprising:
causing transmission of information relating to the rebate claim validation request to a covered entity computer.

15. A computer program product comprising at least one non-transitory computer-readable storage medium having computer-executable program code instructions stored therein, the computer-executable program code instructions comprising program code instructions to:

receive an indication of a rebate claim validation request from a rebate facilitation computer associated with a prescription drug manufacturer, the rebate claim validation request comprising requestor-provided prescription drug information;

receive an indication of a plurality of adjudicated prescription claims received from a plurality of pharmacy computers, wherein an adjudicated prescription claim comprises pharmacy-provided prescription drug information and patient information associated with a patient with whom a respective adjudicated prescription claim is associated;

determine a corresponding adjudicated prescription claim that corresponds with the rebate claim validation request, from the plurality of adjudicated prescription claims, by matching one or more of the requestor-provided prescription drug information to one or more pharmacy-provided prescription drug information;

receive a plurality of encounter records from a healthcare entity computer, an encounter record comprising a medication identifier of a prescribed medication, diagnosis information, and patient information;

generate, by at least accessing the plurality of encounter records received from the healthcare entity computer, and the corresponding adjudication prescription claim received from a prescription claim computer, a discount indicator indicating whether the corresponding adjudicated prescription claim is associated with a discount program; and cause transmission of a rebate claim validation response to the rebate facilitation computer, the rebate claim validation response comprising the discount indicator and information associating the rebate claim validation response to the rebate claim validation request, wherein in an instance the discount indicator indicates a discount was applied, an associated rebate request received from a prescription benefits manager (PBM) computer is automatically rejected by the rebate facilitation computer associated with then prescription drug manufacturer.

16. The computer program product of claim 15, wherein the discount program is the 340B program, and the discount indicator indicates whether or not the corresponding adjudicated prescription claim reflects 340B pricing under the 340B program.

17. The computer program product according to claim 15, wherein generating the discount indicator comprises:

determining whether there are one or more relevant encounter records from the plurality of encounter records that comprise patient information associated with the patient information of the corresponding adjudicated prescription claim, and comprise prescription drug information consistent with the pharmacy-provided prescription drug information of the corresponding adjudicated prescription claim; and in an instance it is determined there are no relevant encounter records from the plurality of encounter records that comprise patient information associated with the patient information of the corresponding adjudicated prescription claim, and comprise prescription drug information consistent with the pharmacy-provided prescription drug information of the corresponding adjudicated prescription claim, generating the discount indicator to indicate the corresponding adjudicated prescription claim is not associated with a discount program.

18. The computer program product according to claim 17, wherein in an instance it is determined there are one or more relevant encounter records from the plurality of encounter records that comprise patient information associated with the patient information of the corresponding adjudicated prescription claim, generating the discount indicator further comprises:
- accessing an eligibility database configured to maintain records comprising associations amongst diagnoses, prescription drug information, and eligibility in a discount program;
- based on the associations amongst diagnoses, prescription drug information, and discount program eligibility, determine whether any of the one or more relevant encounter records are associated with a covered entity and comprise prescription drug information and diagnosis information indicating eligibility under the discount program;
- in an instance one or more of the one or more relevant encounter records are associated with the covered entity comprise prescription drug information and diagnosis information indicating eligibility under the discount program, generating the discount indicator to indicate the corresponding adjudicated prescription claim is associated with a discount program; and
- in an instance none of the one or more relevant encounter records are associated with the covered entity comprise prescription drug information and diagnosis information indicating eligibility under the discount program, generating the discount indicator to indicate the corresponding adjudicated prescription claim is not associated with a discount program.

19. The computer program product according to claim 18, wherein determining whether any of the one or more relevant encounter records are associated with a covered entity comprises determining whether the healthcare entity computer from which the one or more relevant encounter records originated are associated with the covered entity.

20. The computer program product according to claim 18, wherein determining whether any of the one or more relevant encounter records are associated with a covered entity comprises determining whether a prescriber associated with the one or more relevant encounter records is associated with the covered entity.

21. The apparatus according to claim 1, wherein the rebate claim validation request comprising requestor-provided prescription drug information excludes patient information and diagnosis information.

22. The method according to claim 8, wherein the rebate claim validation request comprising requestor-provided prescription drug information excludes patient information and diagnosis information.

23. The computer program product according to claim 15, wherein the rebate claim validation request comprising requestor-provided prescription drug information excludes patient information and diagnosis information.

* * * * *